US009498594B2

(12) United States Patent
McAuley et al.

(10) Patent No.: US 9,498,594 B2
(45) Date of Patent: *Nov. 22, 2016

(54) BREATHING ASSISTANCE APPARATUS

(71) Applicant: Fisher & Paykel Healthcare Limited, Auckland (NZ)

(72) Inventors: Alastair Edwin McAuley, Auckland (NZ); Christopher Earl Nightingale, Auckland (NZ); Aidan Mark Shotbolt, Dunedin (NZ); Stuart Robert Allen Grant, Auckland (NZ); Lewis George Gradon, Auckland (NZ)

(73) Assignee: FISHER & PAYKEL HEALTHCARE LIMITED, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 14/727,757

(22) Filed: Jun. 1, 2015

(65) Prior Publication Data

US 2016/0022945 A1    Jan. 28, 2016

Related U.S. Application Data

(60) Continuation of application No. 13/360,227, filed on Jan. 27, 2012, now Pat. No. 9,044,563, which is a division of application No. 12/784,016, filed on May 20, 2010, now Pat. No. 8,122,887, which is a division of application No. 10/564,998, filed as application No. PCT/NZ2004/000165 on Jul. 27, 2004, now Pat. No. 7,735,487.

(30) Foreign Application Priority Data

Jul. 30, 2003   (NZ) ........................................ 527313

(51) Int. Cl.
*A61M 11/00* (2006.01)
*A61M 16/06* (2006.01)
(Continued)

(52) U.S. Cl.
CPC ..... *A61M 16/0622* (2014.02); *A61M 16/0057* (2013.01); *A61M 16/06* (2013.01);
(Continued)

(58) Field of Classification Search
CPC ........... A61M 16/06; A61M 16/0616; A61M 16/0633; A61M 16/208; A61M 16/0683; A61M 16/0057; A61M 16/0655; A61M 16/0875; A61M 16/0622
USPC ............ 128/204.18, 202.27, 205.25, 206.21, 128/DIG. 26; 2/6.2, 8.2, 9, 410, 424, 425; 5/622, 636–638, 640, 643; 297/392, 297/393
See application file for complete search history.

(56) References Cited

U.S. PATENT DOCUMENTS 5,220,699 A    6/1993 Farris
5,243,971 A    9/1993 Sullivan et al.
(Continued)

FOREIGN PATENT DOCUMENTS

DE    10045183    5/2002
EP    1205205    5/2002
(Continued)

*Primary Examiner* — Steven Douglas
(74) *Attorney, Agent, or Firm* — Knobbe, Martens, Olson & Bear LLP

(57) ABSTRACT

A patient interface that is comfortable for a user to wear is disclosed. The patient interface includes a forehead rest and cushion. In particular the cushion includes a deformable resilient member that when compressed creates a uniformly and gradually increasing force while evenly distributing the pressure on the forehead of the patient.

20 Claims, 10 Drawing Sheets

(51) Int. Cl.
  *A61M 16/00* (2006.01)
  *A61M 16/20* (2006.01)
  *A61M 16/08* (2006.01)

(52) U.S. Cl.
  CPC ..... *A61M16/0616* (2014.02); *A61M 16/0633* (2014.02); *A61M 16/0655* (2014.02); *A61M 16/0683* (2013.01); *A61M 16/0875* (2013.01); *A61M 16/208* (2013.01)

(56) References Cited

U.S. PATENT DOCUMENTS

| | | |
|---|---|---|
| 5,558,090 A | 9/1996 | James |
| 5,570,689 A | 11/1996 | Starr et al. |
| 5,687,715 A | 11/1997 | Landis et al. |
| 6,112,746 A | 9/2000 | Kwok et al. |
| 6,119,693 A | 9/2000 | Kwok et al. |
| 6,467,483 B1 | 10/2002 | Kopacko et al. |
| 6,520,182 B1 | 2/2003 | Gunaratnam |
| 6,805,117 B1 | 10/2004 | Ho et al. |
| 7,000,614 B2 | 2/2006 | Lang et al. |
| 7,219,670 B2 | 5/2007 | Jones et al. |
| 7,234,462 B2 | 6/2007 | Palazzotto et al. |
| 7,296,574 B2 | 11/2007 | Ho et al. |
| 7,503,327 B2 | 3/2009 | Gunaratnam |
| 7,735,487 B2 | 6/2010 | McAuley et al. |
| 8,122,887 B2 | 2/2012 | McAuley et al. |
| 9,044,563 B2 | 6/2015 | McAuley et al. |
| 9,144,656 B2 | 9/2015 | Lang et al. |
| 2003/0066531 A1 | 4/2003 | Gradon et al. |
| 2004/0045550 A1 | 3/2004 | Lang et al. |
| 2004/0045551 A1 | 3/2004 | Eaton et al. |
| 2004/0065328 A1 | 4/2004 | Amarasinghe et al. |
| 2016/0001030 A1 | 1/2016 | McAuley et al. |
| 2016/0067439 A1 | 3/2016 | Kwok |

FOREIGN PATENT DOCUMENTS

| | | |
|---|---|---|
| WO | WO 00/78384 | 12/2000 |
| WO | WO 2004/022145 | 3/2004 |

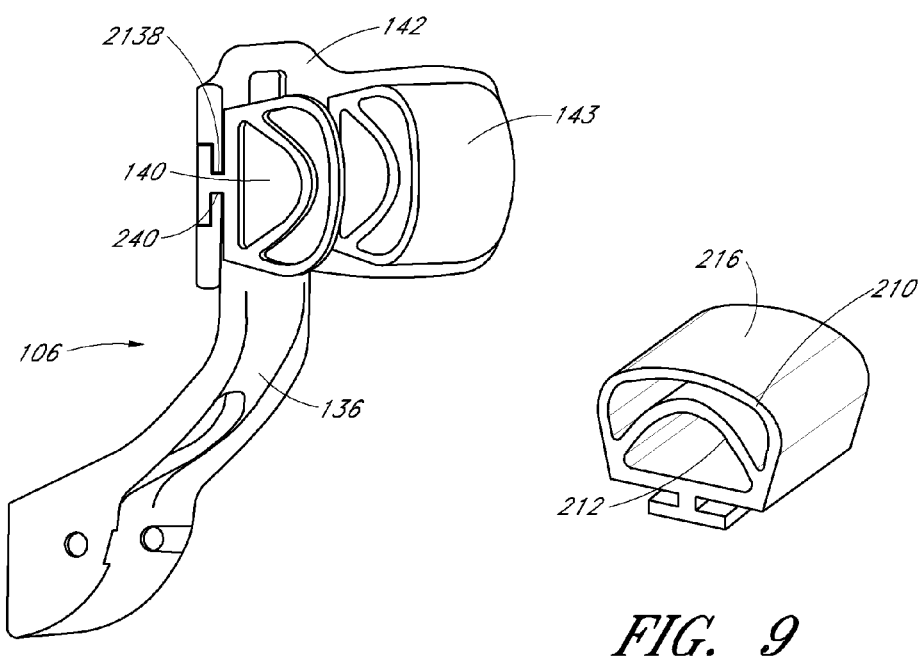
FIG. 7
(PRIOR ART)
FIG. 9
(PRIOR ART)
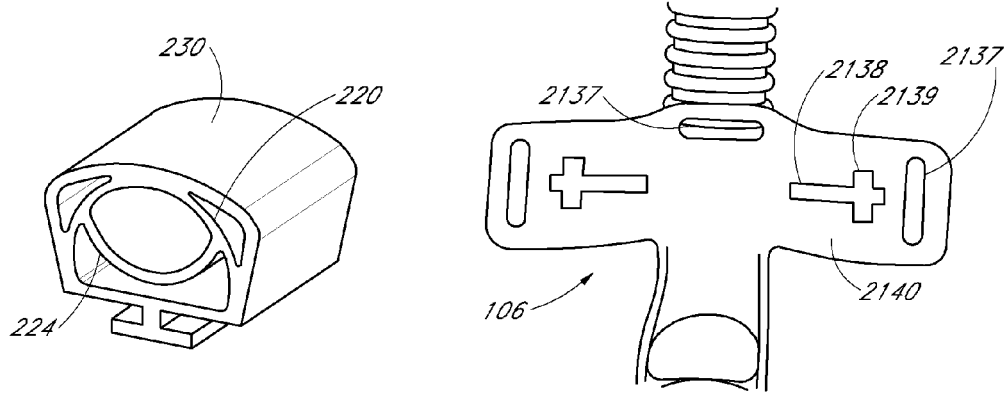
FIG. 11
(PRIOR ART)
FIG. 12
(PRIOR ART)

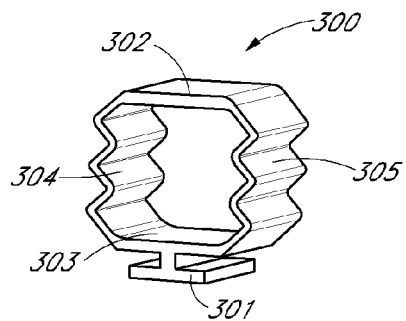
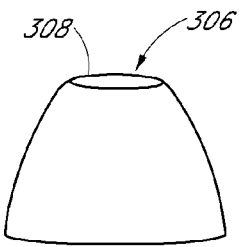
*FIG. 13*  *FIG. 14*
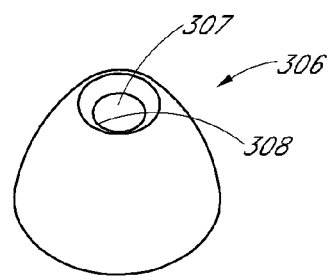
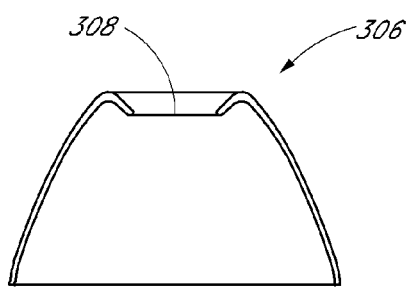
*FIG. 15*  *FIG. 16*
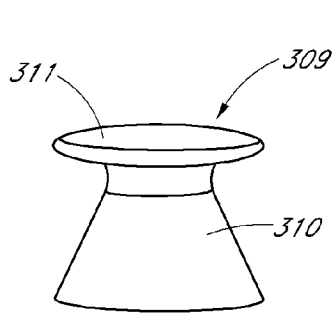
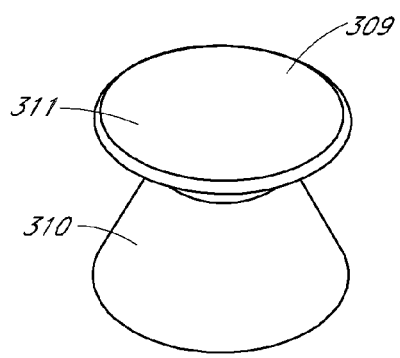
*FIG. 17*  *FIG. 18*

BREATHING ASSISTANCE APPARATUS

CROSS-REFERENCE TO RELATED APPLICATIONS

This application is a continuation application of U.S. patent application Ser. No. 13/360,227, filed Jan. 27, 2012, which is a divisional application of U.S. patent application Ser. No. 12/784,016, filed May 20, 2010 (issued on Feb. 28, 2012 as U.S. Pat. No. 8,122,887), which is a divisional application of U.S. patent application Ser. No. 10/564,998 (issued on Jun. 15, 2010 as U.S. Pat. No. 7,735,487), which received a 371 filing date of Jun. 6, 2006 and is a 371 filing of PCT/NZ2004/000165, filed on Jul. 27, 2004. These applications claim priority from New Zealand Application No. 527313, which was filed on Jul. 30, 2003. All of these references are hereby incorporated by reference in their entirety.

BACKGROUND OF THE INVENTION

Field of the Invention

This invention relates to patient interfaces particularly though not solely for use in delivering Continuous Positive Airways Pressure (CPAP) therapy to patients suffering from obstructive sleep apnoea (OSA). In particular the present invention relates to forehead rest pads on patient interfaces.

Description of the Related Art

In the art of respiration devices, there are well known variety of respiratory masks which cover the nose and/or mouth of a human user in order to provide a continuous seal around the nasal and/or oral areas of the face such that gas may be provided at positive pressure within the mask for consumption by the user. The uses for such masks range from high altitude breathing (i.e., aviation applications) to mining and fire fighting applications, to various medical diagnostic and therapeutic applications.

One requisite of such respiratory masks has been that they provide an effective seal against the user's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

U.S. Pat. No. 5,243,971 and U.S. Pat. No. 6,112,746 are examples of prior art attempts to improve the mask system. U.S. Pat. No. 5,570,689 and PCT publication No. WO 00/78384, and U.S. Pat. No. 6,119,693 are examples of attempts to improve the forehead rest.

SUMMARY OF THE INVENTION

It is an object of the present invention to attempt to provide a patient interface which goes some way to overcoming the abovementioned disadvantages in the prior art or which will at least provide the industry with a useful choice.

Accordingly in a first aspect the present invention consists in a device for delivering a supply of gases to a user comprising:

a patient interface, in use in fluid communication with said supply of gases, a forehead rest engaging said interface including a deformable resilient member configured to in use rest against the face of a patient, said deformable resilient member when compressed in use creating a uniformly and gradually increasing force, while evenly distributing the pressure on the area of the forehead of said patient that contacts said resilient member.

Preferably said deformable resilient member has a top surface and a base connected by two side walls, said side walls being thin and in use are compressible.

Preferably said top surface is substantially thicker than said side walls.

Preferably said top surface includes additional support at its centre to limit its collapse.

Preferably said side walls are capable of folding under compression.

Preferably said deformable resilient member is moulded from silicone.

Alternatively said deformable resilient member is extruded from silicone.

In a second aspect the present invention consists in a device for delivering a supply of gases to a user comprising:

a patient interface, in use in fluid communication with said supply of gases, a forehead rest engaging said interface including a deformable resilient member configured to in use rest against the face of a patient, said deformable resilient member being of a hollow conical shape where in use and under compression the top part of said hollow cone deforms or the side walls of said cone deform.

Preferably said deformable resilient member is moulded from silicone.

Alternatively said deformable resilient member is extruded from silicone.

In a third aspect the present invention consists in a device for delivering a supply of gases to a user comprising:

a patient interface, in use in fluid communication with said supply of gases, a forehead rest engaging said interface, an adjustable deformable resilient member mounted on said forehead rest, said adjustable deformable resilient member configured to in use rest against the face of a patient, said resilient member is height adjustable such that said patient can adjust the distance between said forehead rest and the face of said patient.

Preferably said adjustable deformable resilient member is at least one adjustable strap attached and adjustable on said forehead rest.

Alternatively said adjustable deformable resilient member is a member rotatably mounted on said forehead rest.

In the alternate form the adjustable deformable resilient member being rotatable relative to said forehead rest In a further form said resilient member has two ends, one of the resilient member being fixed to the forehead rest, the other end of the strap is free, said free end capable of sliding relative to said forehead rest, said sliding of free end of strap allowing said user to adjust the height between said forehead rest and said forehead of said user.

Preferably said forehead rest includes a plurality of recesses, the free end of the strap including a slideable sleeve, said slideable sleeve sliding relative to said forehead rest and slideably moving said strap to adjust the height of said resilient member, said sleeve also capable of being fixed into any one of the recesses, said recesses allowing varying degrees of height adjustment.

Preferably said forehead rest also including an aperture, said fixed end of strap fixed to said forehead rest by engaging into said aperture.

Preferably said strap includes a plurality of protrusions at each end, said protrusions at said fixed end of said strap engaging with said aperture to fix said strap to said forehead rest, said protrusions at said free end of said strap engaging with said sleeve to connect said strap to said sliding sleeve.

Preferably said forehead rest is substantially T shaped, said forehead rest comprising two lateral arms extending outward from a vertical arm, said resilient member attached to at least one lateral arm of said forehead rest.

Alternatively said forehead rest is substantially I shaped.

In a further form said strap has a fixed end and a movable end, said fixed end fixed to the forehead rest, said movable end is arranged on said forehead rest to form a substantially circular shape that provides a cushioning effect should a force be applied.

Preferably said movable end of said strap being threaded through an aperture in the arm to form said circular shape, said movable end of said strap being adjustable on said forehead rest to allow a user to adjust the size of the circular shape created by said strap.

Preferably said strap includes a plurality of spaced apart apertures on the strap, said forehead rest including a protrusion extending outward from said forehead rest, said protrusion capable of engaging with any one of said apertures on said strap to fix the movable end of said strap and fix the size of said circular shape, said plurality of spaced apart holes on strap allowing a user to adjust the size of said circular shape.

Preferably said forehead rest includes a holding sleeve, said holding sleeve holding said strap in a substantially correct orientation relative to the forehead rest and protrusion on said forehead rest.

Preferably said forehead rest is a substantially I shaped piece.

In another form said strap is arranged on said forehead rest to form two arced sections relative to said forehead rest, said arced sections resting against a user's head and providing a cushioning effect.

Preferably said forehead rest includes at least one aperture, said strap curled through said aperture to form a middle section extending in the opposing direction to said arced sections.

Preferably said strap is folded back on itself to form said middle section, said strap having two ends, both ends of said strap fixed to opposing ends of said forehead rest.

Preferably said forehead rest includes a lip at each end of said forehead rest, said rest comprising an abutment at each end of said strap, said abutment engaging with said lip to fix each end of said strap to said forehead rest.

Preferably said forehead rest includes a pair of apertures said strap curling through both said apertures to form said middle section and arced sections.

Preferably said middle section can be pulled through or pushed through said aperture or apertures in order to increase or decrease the size of said arced sections.

Preferably said strap includes a plurality of spaced apart notches along the edge of said strap, said notches capable of engaging with said aperture or apertures to hold said middle section in place, said notches providing incremental positions for the middle section to be held and said notches providing incremental sizes of said arced sections.

Preferably said strap has notches along both edges of said strap to provide for better grip and engagement with said aperture or apertures.

BRIEF DESCRIPTION OF THE DRAWINGS

One preferred form of the present invention will now be described with reference to the accompanying drawings, FIG. 7 shows a prior art forehead rest in isolation, FIG. 9 shows a perspective view of the forehead rest cushion of FIG. 7, FIG. 11 is a section of perspective view of the forehead rest cushion of FIG. 10, FIG. 12 is a back view showing the slots in the forehead rest for each cushion to lock into, FIG. 13 is a perspective view of a first embodiment of a forehead rest cushion of the present invention, FIG. 14 is a perspective view of a second embodiment of a forehead rest cushion of the present invention, FIG. 15 is an alternative perspective view of the forehead rest cushion of FIG. 14, FIG. 16 is a section of the forehead rest cushion of FIG. 14, FIG. 17 is a side view of a third embodiment of a forehead rest cushion of the present invention, FIG. 18 is an alternative perspective view of the forehead rest cushion of FIG. 17.

DETAILED DESCRIPTION OF THE PREFERRED EMBODIMENT

The present invention provides improvements in the delivery of humidified gases therapy. In particular a patient interface is described which is more comfortable for the user to wear and reduces leakage as compared with the prior art. It will be appreciated that the patient interface as described in the preferred embodiment of the present invention can be used in respiratory care generally or with a ventilator but will now be described below with reference to use in a humidified CPAP system. It will also be appreciated that the present invention can be applied to any form of patient interface including, but not limited to, nasal masks, oral masks and mouthpieces.

Figure 1:
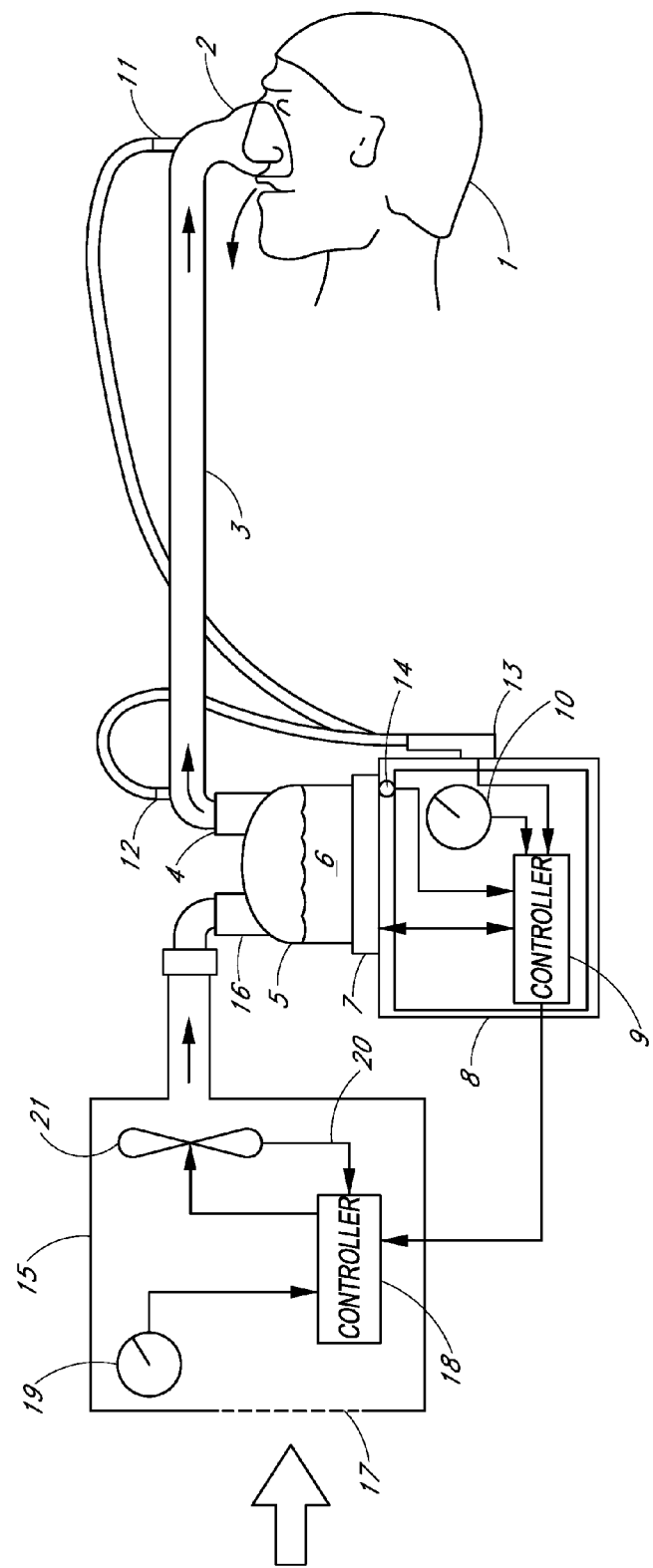
FIG. 1 is a block diagram of a humidified continuous positive airway pressure (system) as might be used in conjunction with the present invention.

With reference to FIG. 1 a humidified Continuous Positive Airway Pressure (CPAP) system is shown in which a patient 1 is receiving humidified and pressurised gases through a patient interface 2 connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. Inspiratory conduit 3 is connected to the outlet 4 of a humidification chamber 5 which contains a volume of water 6. Inspiratory conduit 3 may contain heating means or heater wires (not shown) which heat the walls of the conduit to reduce condensation of humidified gases within the conduit. Humidification chamber 6 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (preset value) of humidity or temperature of the gases supplied to patient 1. The controller may also receive input from other sources, for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. Exhaled gases from the patient's mouth are passed directly to ambient surroundings in FIG. 1.

Figure 2:
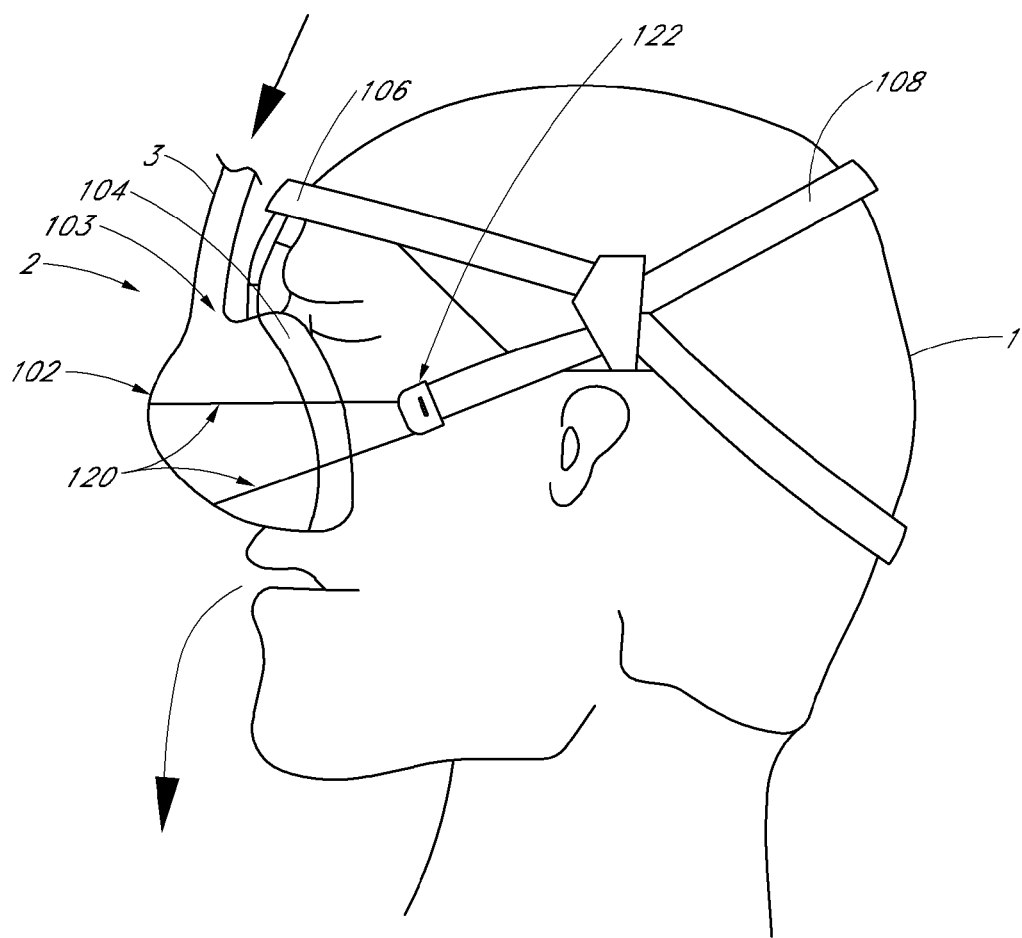
FIG. 2 is an illustration of the nasal mask in use according to the preferred embodiment of the present invention.

Blower 15 is provided with variable pressure regulating means or variable speed fan 21 which draws air or other gases through blower inlet 17. The speed of variable speed fan 21 is controlled by electronic controller 18 (or alternatively the function of controller 18 could carried out by controller 9) in response to inputs from controller 9 and a user set predetermined required value (preset value) of pressure or fan speed via dial 19. Nasal Mask According to a first embodiment of the present invention the patient interface is shown in FIG. 2 as a mask. It will be appreciated the patient interface could equally be a nasal mask, full face, oral mask or mouth piece, endotracheal tube or cannula by way of example. The mask includes a hollow body 102 with an inlet 103 connected to the inspiratory conduit 3. The mask 2 is positioned around the nose of the user 1 with the headgear 108 secured around the back of the head of the patient 1. The restraining force from the headgear 108 on the hollow body 102 and the forehead rest 106 ensures enough compressive force on the mask cushion 104, to provide an effective seal against the patient's face.

The hollow body 102 is constructed of a relatively inflexible material for example, polycarbonate plastic. Such a material would provide the requisite rigidity as well as being transparent and a relatively good insulator. The expiratory gases can be expelled through a valve (not shown) in the mask, a further expiratory conduit (not shown), or any other such method as is known in the art.

Mask Cushion

Figure 3:
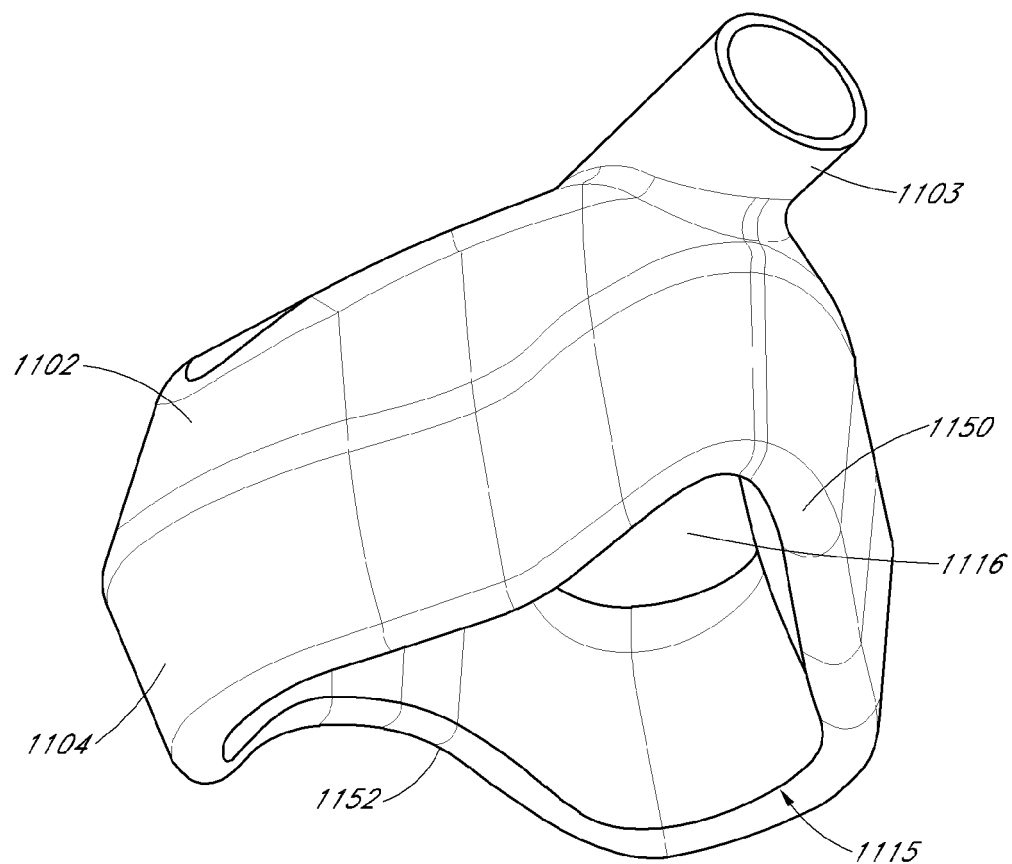
FIG. 3 shows a perspective view of the mask with cushion.
Figure 4:
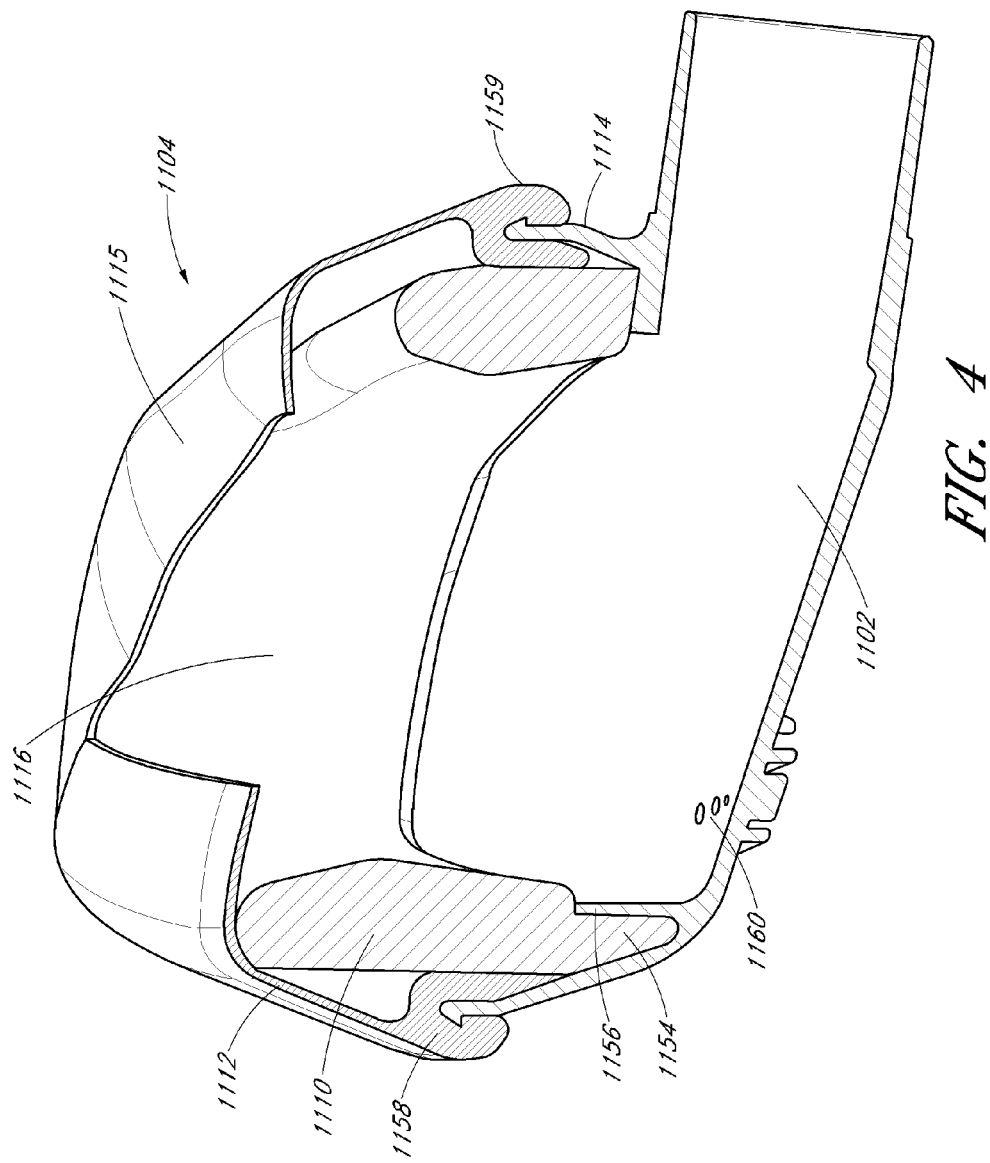
FIG. 4 is a cutaway view of the mask showing the cushion.

Referring now to FIGS. 3 and 4 in particular, the mask cushion 1104 is provided around the periphery of the nasal mask 1102 to provide an effective seal onto the face of the user to prevent leakage. The mask cushion 1104 is shaped to approximately follow the contours of a patient's face. The mask cushion 1104 will deform when pressure is applied by the headgear 1108 to adapt to the individual contours of any particular user. In particular, there is an indented section 1150 intended to fit over the bridge of the user's nose as well as a less indented section 1152 to seal around the section beneath the nose and above the upper lip.

In FIG. 4 we see that the mask cushion 1104 is composed of a inner foam cushion 1110 covered by an outer sealing sheath 1112. The inner cushion 1110 is constructed of a resilient material for example polyurethane foam, to distribute the pressure evenly along the seal around the user's face. The inner cushion 1110 is located around the outer periphery 1114 of the open face 1116 of the hollow body 1102. Similarly the outer sheath 1112 may be commonly attached at its base 1113 to the periphery 1114 and loosely covers over the top of the inner cushion 1110.

In the preferred embodiment shown in FIGS. 3-6 the bottom of the inner cushion 1110 fits into a generally triangular cavity 1154 in the hollow body 1102. The cavity 1154 is formed from a flange 1156 running mid-way around the interior of the hollow body.

Figure 5:
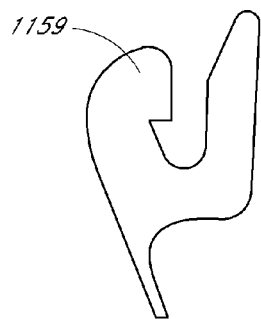
FIG. 5 is a cutaway view of the periphery of the outer membrane.
Figure 6:
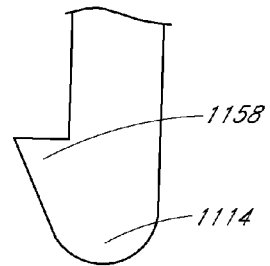
FIG. 6 is a cutaway view of the periphery of the mask body portion.

The outer sheath 1112 fits in place over the cushion 1110, holding it in place. The sheath 1112 is secured by a snap-fit to the periphery 1114 of the hollow body. In FIGS. 5-6 the periphery 1114 is shown including an outer bead 1158. The sheath 1112 includes a matching bead 1159, whereby once stretched around the periphery, the two beads engage to hold the sheath in place.

Forehead Rest

A prior art nasal mask 102 including a forehead rest 106 is shown in FIGS. 2 and 7. The forehead rest 106 may move freely in proximity to the mask body 102 and user, but with no lateral movement or may be permanently fixed or adjustably fixed.

Referring to FIG. 7, at the top end 142 (around the user's forehead) of the bridge member 136 harnessing slots (not shown) are provided which allow straps from the headgear to be inserted to secure the mask to the headgear. For the user's comfort one or more resilient cushions 140 are provided on the T-piece of the forehead rest 142 the top end of the bridge member 136, to rest on the forehead of the user. The cushion 140 is constructed by injection moulding or extruding, from silicone or any foam materials as is known in the art for providing cushioning. In FIG. 7 a second cushion 143 is shown at the other end of the section 142.

Forehead Rest Cushion

Figure 8:
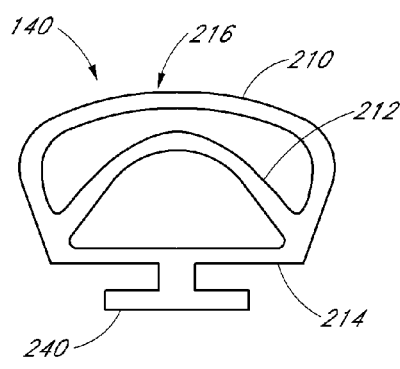
FIG. 8 shows a section view of the prior art forehead rest of FIG. 7.

Referring now to FIGS. 8 and 9 the prior art forehead rest cushion 140 is illustrated. The cushion 140, in cross section, includes an outer curved member 210 and a inner curved member 212 both of which are attached at each end to a straight base member 214. The inner curved member 212 is a substantially similar curved shape to the outer curved member 210. The inner member 212 and outer member 210 may be coterminous, the inner member may attach to the outer member 210 or both may attach to the base 214 separately.

When the cushion 140 comes into contact with the user's face the outer curved member 210 deforms as more pressure is applied to the cushion towards the face. This comprises of the first mode of deformation. Once the outer curved member 210 deforms enough to contact the inner curved member a second mode of deformation occurs.

As will be appreciated if the outer curved member is flatter than the second curved member 212 the first mode requires less force. The relative curvature and thickness of each can be varied to give a characteristic first mode and second mode. Once in the second mode of deformation extra force is required to deform both the first curved member 210 and the second curved member 212. This configuration described above results in more even deformation force across the load bearing surface of the cushion 216 and also results in a more progressive force of cushioning when the cushion 120 is deformed.

Figure 10:
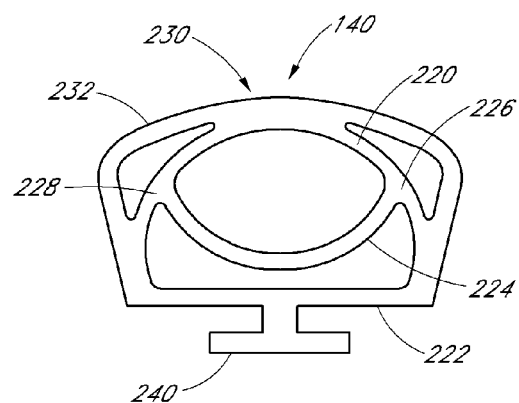
FIG. 10 is a section of a further prior art forehead rest cushion.

A further prior art embodiment of a forehead rest cushion is shown in FIGS. 10 and 11. This forehead rest cushion 140 has an outer curved member 220 attached at either end to a straight base member 222. A inner inverted curved member 224 is inverted with respect the outer curved member 220 and is attached at either end two points on the 226, 228 on the outer curved member 220. The inner inverted curved member is lower in overall height than the outer curved member 220 such that a first mode of deformation occurs when the outer curved member 220 is deformed. A second mode of deformation occurs when the inner inverted curved member 224 contacts the base member 222. The outer curved member 220 and the inner inverted curved member 224 deform simultaneously. The forces across the load bearing surface 230 are further distributed by virtue of a generally quadrilateral member 232 including as one side the base member 222 which attaches over the inner inverted curved member 220 approximately at its ends and at its load bearing point 234. The quadrilateral member 232 provides additional stiffness and reduces lateral deformation.

These prior art forehead rests have a base member that includes a flange 240 which engages with a slot 2138 in the forehead rest 106 to lock the forehead rest cushion in place. The flange 240 first slides through aperture 2139 as seen in FIG. 12.

In the preferred forms of the forehead rest cushion of the present invention will now be described with reference to FIGS. 13 to 26, 31 and 32. With each of the embodiments as described in relation to these figures the forehead rest cushion or pad allows for a controlled compression of the cushion. Each cushion is capable of being compressed under a force and will return to its original position (as shown in the Figures) when the force ceases.

A first embodiment of the forehead rest cushion is shown in FIG. 13. This forehead rest cushion 300 has a flange 301 that is able to be attached to a forehead rest, such as that rest 106 shown in FIG. 7 or 12. The flange 301 slides through the aperture 2139 in the T-piece 2140 of the forehead rest 106. The cushion 300 is substantially rectangular in shape with an upper wall 302 and lower wall 303, with the flange being attached to the lower wall 303. The side walls are corrugated or concertinaed such that these walls 304, 305 collapse when a force is placed on the upper wall 302. As described above, as the cushions are made from a plastics material, such as silicone or foam, the folds forming the side walls will return to the original form when any compression force ceases.

FIG. 14 shows a second embodiment of a forehead rest cushion of the present invention. This forehead rest cushion 306 is a cushion that is in the general shape of a parabolic cone. The cushion has an open top 307 that can be seen in FIG. 15, this open top 307 allows the edge 308 of the cushion 306 to roll inwards when the top of the cone shaped cushion is compressed, or a force placed air on. This cushion may be attached to a forehead rest, such as the T-piece forehead rest as shown in FIGS. 7 and 12 by any appropriate means, for example, gluing or the like and may include a flange such as that described above with reference to FIG. 13.

In alternative embodiments any of the forehead rest cushion of the present invention as shown in the Figures may have an alternative attachment mechanism such as an arrow head type barb or protrusion, which fits into apertures on the forehead rest. Alternatively, any of the cushions may be provided with an aperture in place of the flange that is able to be slid about an arm of the forehead rest.

Figure 19:
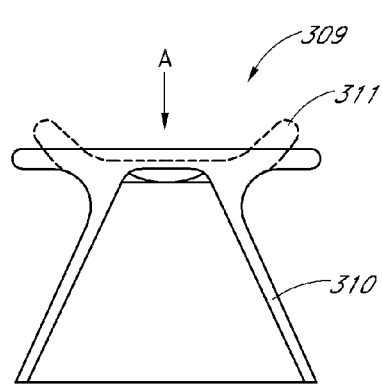
FIG. 19 is a section view of the forehead rest cushion of FIG. 17.

A third embodiment of the forehead rest cushion of the present invention is shown in FIGS. 17, 18 and 19. This cushion 309 has a conical body 310 with a flattened circular top 311. This cushion is either injection moulded, extruded, or stamped from a sheet of material and is preferably made of a thermoplastic elastomer, silicone or foam. Again, when a force is applied to the top 311 the inner areas of the top roll inwards down towards the top of the cone body 310. For example, as shown in FIG. 19 in a section view when a force A is placed on the top 311 the inner area of the top 311 moves downwards and the outer areas, shown as 311', move upwards or simply adjust to the shape of the area of user's forehead it abuts.

Figure 20:
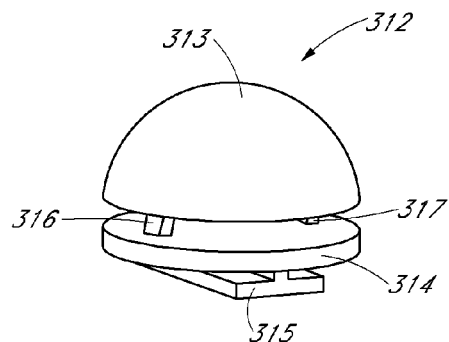
FIG. 20 is a perspective view of a fourth embodiment of a forehead rest cushion of the present invention.
Figure 21:
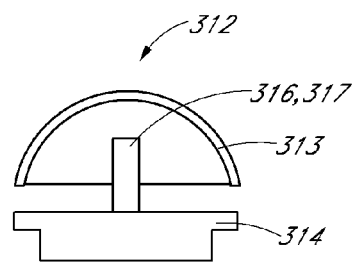
FIG. 21 is a section of the forehead rest cushion of FIG. 20.

Reference is now made to FIGS. 20 and 21 where the force embodiment of the forehead rest cushion of the present invention is shown this forehead rest cushion 312 is of a hemispherical shape and also allows for a two stage cushioning when a force is placed upon it. The cushion 312 has a hemispherical body 313 suspended above a platform 314 and also has a flange 315 allowing the cushion 312 to be slotted into an aperture in a forehead rest, such as that described above. The hemispherical body 313 is suspended above platform 314 on small supports 316, 317. This cushion 312 is preferably moulded from a thermoplastics material, silicone or foam.

Figure 22:
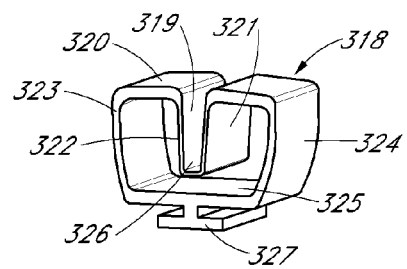
FIG. 22 is a perspective view of a fifth embodiment of a forehead rest cushion of the present invention.

A fifth embodiment of the forehead rest cushion is shown in FIG. 22. The cushion 318 is shaped in the form of an "M" or generally rectangular with a recess 319 formed in the top wall 320 of the cushion 318. Therefore, two inner vertical walls 321, 322 are formed parallel to the outer vertical walls 323, 324. When a force is applied to the upper wall 320 the recessed part 319 and vertical walls 322, 321 are pushed downwards towards the lower wall 325. When the apex 326 of the recessed part 319 hits the lower wall 325 the cushion may still be compressed, but at a different rate of force such that the compression of this cushion 318 is a two stage compression. The recess 319 in the middle of the cushion 318 therefore provides more uniform pressure across the top wall 320 of the cushion. As with other forms as described above this forehead cushion 318 is supplied with a flange 327 attached to the lower wall 325 allowing the cushion 318 to be attached to the forehead rest.

Figure 23:
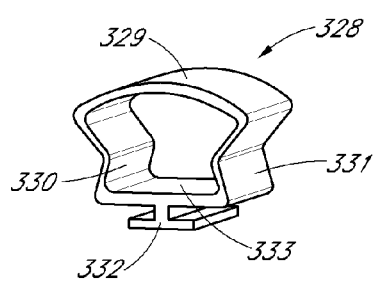
FIG. 23 is a sixth embodiment of a forehead rest cushion of the present invention.

Reference is now made to FIG. 23 where a sixth embodiment of the forehead rest cushion of the present invention is shown. This cushion 328 is of a similar form to that described in relation to FIG. 13, but its top or upper wall 329 is curved and the side walls 330, 331 merely form one corrugation or fold. When a force is placed upon the upper wall 329 the side walls 330, 331 fold in upon themselves. Again, this cushion has a flange 332 attached to its lower wall 333 to allow the cushion 328 to be attached to the forehead rest.

Figure 24:
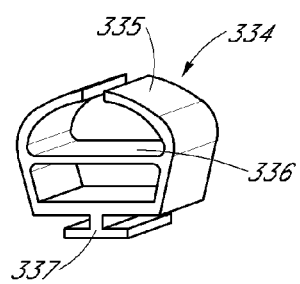
FIG. 24 is a seventh embodiment of a forehead rest cushion of the present invention.

A seventh embodiment of the forehead rest cushion as shown in FIG. 24, this cushion is very similar in form to that of the prior art cushion as shown in FIG. 8 but its upper wall 335 is split in two and its inner wall 336 is horizontal in nature and not curved. Again, this cushion 334 has a flange 337 that allows it to be attached to a forehead rest. This cushion provides a two stage compression where the inner wall provides stability to the cushion 334.

Figure 25:
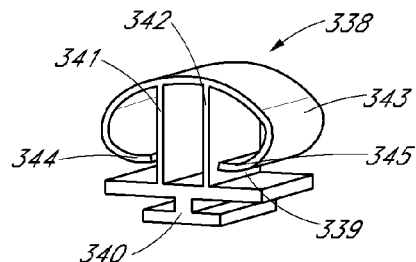
FIG. 25 is a perspective view of an eighth embodiment of a forehead rest cushion of the present invention.

The eighth embodiment of the forehead rest cushion of the present invention is shown in FIG. 25. This cushion 318 has a base member 319 having a flange similar to as described above in relation to the prior art cushions. The flange 340 allows the cushion 338 to be attached to a forehead rest. Two vertical walls 341, 342 extend upwards nearer the centre of the base member 339, and a curved upper member in the shape of a partial oval is attached above the vertical walls 341, 342. When a force is placed on the curved upper member 343 the vertical walls 341, 342 initially support the force placed on the upper member 343. The outer edges 344, 345 of the upper member 343 are able to freely roll inwards to give further controlled support to the cushion 338.

Figure 26:
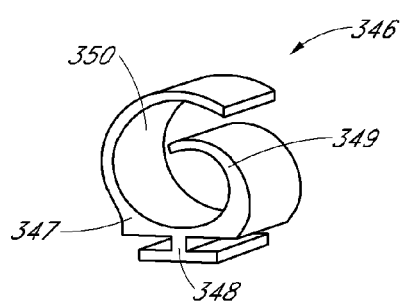
FIG. 26 is a perspective view of a ninth embodiment of a forehead rest cushion of the present invention.

A ninth embodiment of the forehead rest cushion of the present invention is shown in FIG. 26. This cushion 346 has a base member 347 and a flange attached to it to enable the cushion to be attached to a forehead rest. Extending outwards and upwards from the edges of the base member 347 are arms 349, 350. These arms 349, 350 are curved inwardly towards one another and may overlap. When a force is placed on the upper 350 arm, the arm 350 moves down towards the lower arm 349. If enough force or a continued force is provided to the upper arm 350, the upper arm 350 will continue to compress against and push the lower arm 349 towards the centre of the cushion 346 and the base member 347. These independent inwardly rolled arms 349, 350 allow for a two stage compression that is controlled when a force being placed on the upper arm 350.

Figure 31:
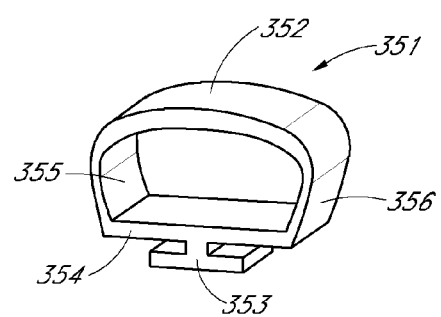
FIG. 31 is a perspective view of a fourteenth embodiment of a forehead rest cushion of the present invention.

A fourteenth embodiment forehead rest cushion of the present invention is shown in FIG. 31. This cushion 351 has a similar shape to the prior art cushion of FIG. 9 and includes a base member 354 and a flange 353 which engages with a slot 2138 in the forehead rest to lock the forehead rest cushion in place. The flange 353 slides through and fixes in the aperture 2139 as seen in FIG. 12. The cushion 351 is substantially rectangular in shape but with an upper wall 352 that is slightly curved at its edges where it meets the side walls 355, 356 of the cushion. The upper wall is thicker in width than the side walls 355, 356 to provide additional strength and control to the cushion. Furthermore, the relative thickness of the upper wall 352 compared to the side walls 355, 356 prevents the cushion 351 from caving in. This helps provide a uniform pressure on the user's forehead.

Figure 32:
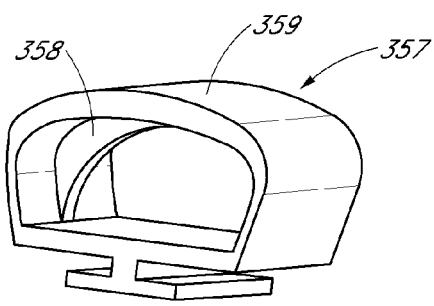
FIG. 32 is a perspective view of a fifteenth embodiment of a forehead rest cushion of the present invention.

A further embodiment of a forehead rest cushion is shown in FIG. 32. This cushion 357 is exactly the same shape as that cushion of FIG. 31, but this cushion has an additional curved short wall 358 extending below and following the contour of the upper wall 359. This short wall 358 provides for additional support to the upper wall 359 when a force is placed upon it.

FIGS. 27 to 30 and 33 illustrate forehead rest cushions that can be adjusted to a user's preference. Firstly referring to FIG. 27 a rotating substantially circular or cam shaped cushion 360 rotatably mountable between two legs 361, 362, which are each attached and extend outwards from the forehead rest or mask base, for example, one on either side of the T-piece as shown in FIG. 12. As the cushion 360 rotates in the direction of Arrow B the offset is increased or decreased.

Figure 27:
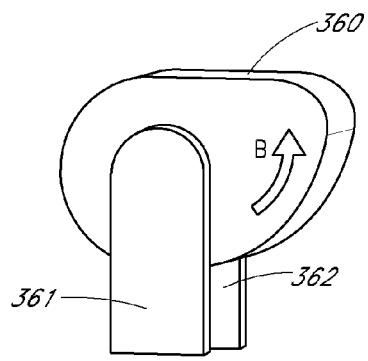
FIG. 27 is a perspective view of a tenth embodiment of a forehead rest cushion of the present invention, where the forehead rest cushion is adjustable to a user's requirements.
Figure 28:
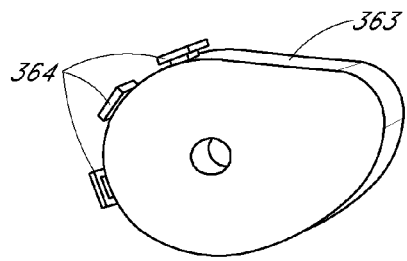
FIG. 28 is a perspective view of an eleventh embodiment of a forehead rest cushion of the present invention, this embodiment also being incapable of being adjusted by the user.

FIG. 28 shows a further embodiment of the cushion of FIG. 27. This cushion 363 additionally has a plurality of fixed attachments 364, similar to the flange on the cushions described above. Each of these can be attached to the forehead support in turn to provide an adjustable cushion.

Figure 29:
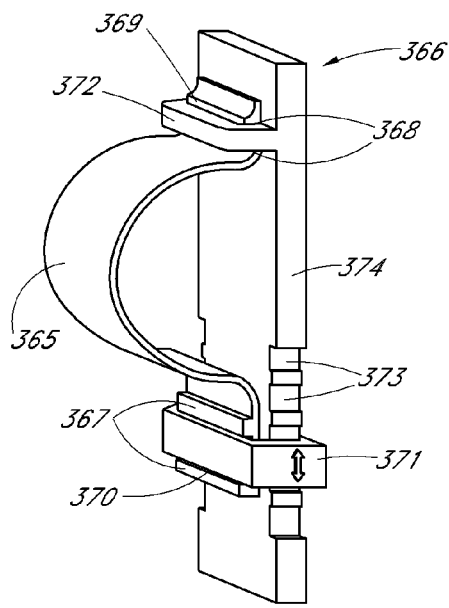
FIG. 29 is a perspective view of a twelfth embodiment of the forehead rest cushion of the present invention, where the forehead rest cushion is adjustable.

A twelfth embodiment of a forehead rest cushion of the present invention is shown in FIG. 29. This cushion 365 is effectively a strap or flexible elongate member (preferably made of a flexible plastics material) attached to one arm 366 of a T or to an I piece of a forehead rest. In the case of a T-shaped forehead rest, such as that shown in FIG. 12, two cushions of this type would be provided one for each of the two arms of the T-shaped forehead rest. The strap 365 is provided with a pair of protrusions 367, 368 at each of its ends 369, 370 such that a recess is formed between each set of protrusions. Each end 369, 370 is fixed to the arm 366 by appropriate means, such as a sleeve 371 or aperture 372 on the arm 366. In particular, the upper end 369 of the strap 365 is fixed to the arm 366 in the aperture 372 and the lower end 370 is slideably adjustable by way of a slideable sleeve 371 capable of sliding and being fixed into any one of a number of recesses 373 formed on the edge 374 of the arm 366.

Figure 30:
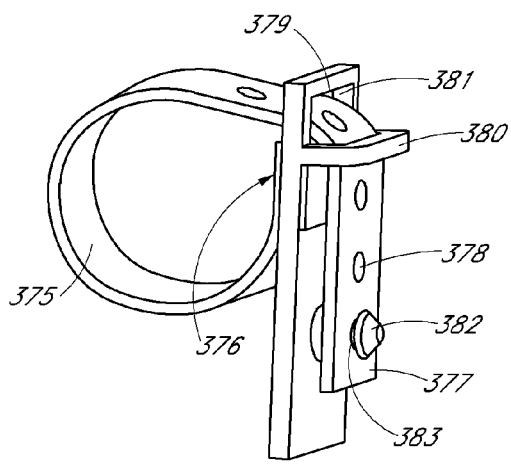
FIG. 30 is a perspective view of a thirteenth embodiment of a forehead rest cushion of the present invention, this embodiment also being adjustable.

A further embodiment of an adjustable forehead rest cushion is shown in FIG. 30. This adjustable cushion 375 is a strap or flexible elongate member where a first end 376 of its two ends 376, 377 is fixed to an arm 379 (similar to that arm 366 described above). The second end 377 of the two ends is threaded about and around such that a substantial part of the strap forms a circular shape that provides a cushioning effect should a force be placed upon it. The second end 377 after being threaded through an aperture 381 in the arm 379, and possibly an further holding sleeve 380 formed on the arm 379, is fixed to the other side of the arm 379, for example by pressing a protrusion 382 through a hole 383 formed in the strap 375. The size of the circular cushion formed can be adjusted as a plurality of spaced apart holes are provided in the strap and the strap can be pulled through the arm and the protrusion 382 fixed in each hole dependent on the requirements of the user.

Figure 33:
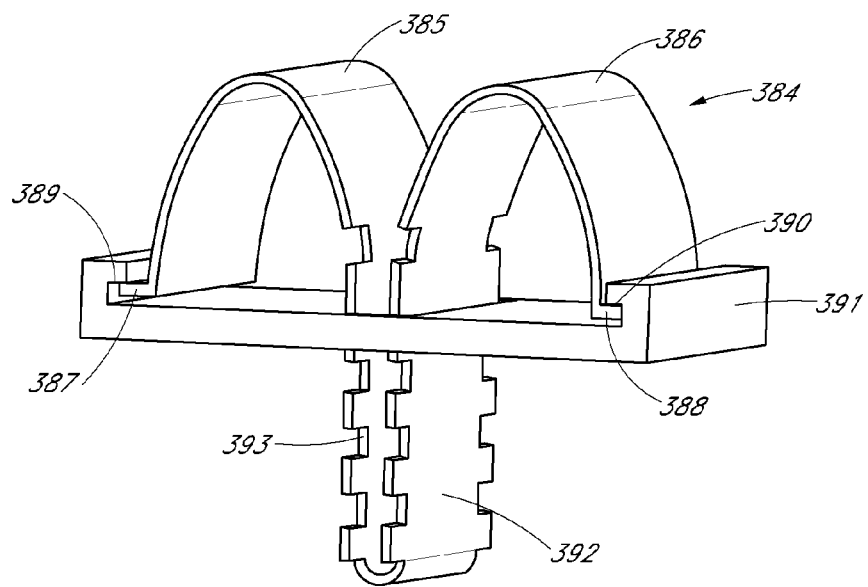
FIG. 33 is a perspective view of a sixteenth embodiment of a forehead rest cushion of the present invention.

Yet still a further embodiment of an adjustable forehead rest cushion is shown in FIG. 33, where a double loop strap 384 is formed into two arced cushions 385, 386. Each of the apexes of the arced cushions 385, 386 would in use rest against a user's forehead to provide additional comfort while wearing a mask or interface similar to that described above. The strap 384 has abutments 387, 388 formed at each end that fit under lips 389, 390 formed in an arm 391 (such as, a one T-piece arm of the forehead rest as described above in relation to FIG. 12, or an I shaped forehead rest as is known in the prior art and particularly described in New Zealand patent application number 524439 of Fisher & Paykel Healthcare Limited). The middle section 392 of the strap 384 has a plurality of notches 393 cut in each of its edges. The strap 384 is threaded through two apertures formed in the middle of the arm 391, such that a substantial portion of the middle section 392 extends out from the arm 391 in an opposing direction to the arced cushions 385, 386. The middle section 393 can be pulled further through the arm or to pushed back through the apertures in the arm using the notches 393 as incremental positions for the middle section to be held in, to decrease or increase the size of the arced cushions 385, 386.

The forehead rest cushion embodiments shown in FIGS. 27 to 30 and 33 are all user adjustable. In particular the forehead rest cushions shown in these figures are height adjustable and allow the user to adjust the amount cushioning the forehead rest cushions can provide. The height of the forehead rest cushion is the distance between the forehead rest 106 and the face or forehead of the user. The height adjustable forehead rest cushion allows a user to adjust the distance between the forehead rest and the lace of the patient. This allows a user to adjust the amount of cushioning provided by the forehead rest cushion.

In other forms of the forehead rest cushion of the present invention the cushion may be an inflatable member that can be manually inflated using a syringe or a hand or finger operated compression pump, or automatically inflated using a compressible reservoir or the like.

What is claimed is:

1. A mask for a respiratory device configured to be positioned around a nose of a user and secured around a back of a head of the user by headgear, the mask comprising:
    a hollow body provided with an inlet configured to be connected to an inspiratory conduit;
    a mask cushion provided around a periphery of the hollow body and configured to follow contours of a face of the user to provide a seal configured to prevent leakage,
        wherein the mask cushion is configured to deform when pressure is applied by the headgear to adapt to the contours of the face of the user, and
        wherein the mask cushion includes an indented section configured to extend over a bridge of the nose of the user and a less indented section configured to seal around an area beneath the nose and above an upper lip of the user,
        wherein the mask cushion includes an inner cushion covered by an outer sealing cushion; and
    a forehead rest which engages the hollow body, the forehead rest including two lateral arms extending outward from a vertical arm,
        wherein the forehead rest includes slots which allow straps from the headgear to be inserted to secure the forehead rest to the headgear,
        wherein the two lateral arms of the forehead rest each include a resilient wall extending away from the vertical arm configured to rest on the face of the user, each resilient wall extending away from the other resilient wall, and
        wherein the resilient walls are configured to space the vertical arm of the forehead rest a distance from the face of the user, a recess being defined at least in part by the two resilient walls at a position adjacent a top portion of the vertical arm of the forehead rest, between the two resilient walls.

2. A mask for a respiratory device configured to extend around a nose of a user and secured around a back of a head of the user by headgear, the mask comprising:
    a hollow body including an inlet configured to be connected to an inspiratory conduit;
    a mask cushion provided around a periphery of the hollow body and configured to provide a seal onto a face of the user to prevent leakage,
        wherein the mask cushion is configured to follow contours of the face of the user,
        wherein the mask cushion is configured to deform when pressure is applied by the headgear to adapt to the contours of the face of the user, and
        wherein the mask cushion includes an inner cushion covered by an outer seal, wherein the inner cushion is comprised of a resilient material configured to distribute pressure evenly along the outer seal around the face of the user; and
    a forehead rest which engages the mask, the forehead rest including two lateral arms extending outward from a vertical arm,
        wherein the forehead rest includes slots which allow straps from the headgear to be inserted to secure the mask to the headgear, and
        wherein the two lateral arms of the forehead rest space the forehead rest a distance from the face of the user.

3. The mask of claim 2 further comprising headgear, wherein the headgear includes a pair of upper forehead straps each of which is configured to extend over part of the forehead of the user and is configured to be received in respective slots on the forehead rest.

4. The mask of claim 3 wherein the headgear includes a pair of lower front straps located below the upper forehead straps and configured to extend over a portion of the cheeks of the user, the lower front straps configured to be secured to the mask through a pair of lower slots, wherein the lower slots are located below the slots in, the forehead rest.

5. The mask of claim 4 wherein the upper and lower front straps of the headgear extend from a pair of junction members configured to be adjacent to the ears of the user.

6. The mask of claim 3 wherein the headgear includes an upper rear strap which is configured to extend around an upper part of the head of the user.

7. The mask of claim 6 wherein the upper forehead straps and the upper rear strap extend from a position above the ears of the user.

8. The mask of claim 6 further including a lower rear strap located below the upper rear strap, wherein the lower rear strap is configured to extend around a lower part of the rear of the head of the user.

9. The mask of claim 7 wherein the upper and lower rear straps of the headgear extend from a pair of junction members adjacent to the ears of the user.

10. The mask of claim 3 wherein the straps of the headgear each include a loop, the loop of each strap configured to be received in a respective slot on the forehead rest and/or the mask.

11. The mask of claim 10 wherein the loops of one or more straps of the headgear are adjustable.

12. The mask of claim 2 further comprising headgear provided with a pair of upper forward straps configured to connect to respective slots on the forehead rest, and a pair of lower forward straps configured to connect to respective slots on the mask, the upper forward straps and the lower forward straps configured to extend in front of the ears of the user.

13. The mask of claim 2 wherein the mask cushion includes an indented section configured to extend over a bridge of the nose of the user, and a less indented section configured to seal around a region beneath the nose and above an upper lip of the user.

14. The mask of claim 2 wherein a cavity of the hollow body is generally triangular.

15. The mask of claim 2 wherein the hollow body includes an open face, the inner cushion being located around an outer periphery of the open face of the hollow body, the outer seal being commonly attached at its base to the outer periphery of the open face of the hollow body, the outer seal loosely covering over a top of the inner cushion.

16. The mask of claim 2 including a mask shell which supports the inner cushion and the outer seal, the mask shell including a mask inlet configured to be connected to a breathing conduit.

17. The mask of claim 16 wherein the mask cushion includes a plurality of bias flow holes through the mask shell.

18. The mask of claim 2 wherein the lateral arms of the forehead rest are attached to the forehead rest, the lateral arms of the forehead rest provided with at least one slot through which the material of the forehead rest is received.

19. The mask of claim 2 wherein the forehead rest includes a forehead rest cushion of hemi-spherical shape, which allows for a two stage cushioning when a force is placed upon it.

20. A mask for a respiratory device configured to be positioned around a nose of a user and secured around a back of a head of the user by headgear, the mask comprising:
   a hollow body provided with an inlet configured to be connected to an inspiratory conduit;
   a mask cushion provided around a periphery of the hollow body and configured to follow the contours of a face of the user to provide a seal to prevent leakage,
      wherein the mask cushion is configured to deform when pressure is applied by the headgear to adapt to the contours of the face of the user,
      wherein the mask cushion includes a section configured to fit over a bridge of a nose of the user and a section configured to seal around an area beneath the nose and above an upper lip of the user, and
      wherein the mask cushion includes an inner cushion covered by an outer sealing cushion; and
   a forehead rest which engages an interface, the forehead rest including a pair of laterally spaced slots which allow straps from the headgear to be inserted to secure the mask to the headgear at opposite sides of the forehead rest,
      wherein the forehead rest further includes two arced sections, the arced sections configured to extend against the head of the user and providing a cushioning effect,
      wherein each arced section includes an arm extending laterally from an upper portion of the forehead rest adjacent a longitudinal axis of the forehead rest, and
      wherein each arced section is spaced from the forehead rest by respective arms such that the arced sections space the forehead rest from the face of the user.

\* \* \* \* \*

UNITED STATES PATENT AND TRADEMARK OFFICE
CERTIFICATE OF CORRECTION

PATENT NO. : 9,498,594 B2
APPLICATION NO. : 14/727757
DATED : November 22, 2016
INVENTOR(S) : McAuley et al.

It is certified that error appears in the above-identified patent and that said Letters Patent is hereby corrected as shown below:

In the Specification

In Column 6 at Line 6, After "19." delete "Nasal Mask" and insert the same on Column 6, Line 7, as a new heading.

In the Claims

In Column 12 at Line 41, In Claim 4, change "in," to --on--.

Signed and Sealed this
Twenty-eighth Day of March, 2017

Michelle K. Lee
*Director of the United States Patent and Trademark Office*